United States Patent [19]

Rich, Jr. et al.

[11] 4,314,823

[45] Feb. 9, 1982

[54] COMBINATION APPARATUS AND METHOD FOR CHROMATOGRAPHIC SEPARATION AND QUANTITATIVE ANALYSIS OF MULTIPLE IONIC SPECIES

[75] Inventors: William E. Rich, Jr., Mountain View; Frank C. Smith, Felton; Janet L. McNeill, Sunnyvale, all of Calif.

[73] Assignee: Dionex Corporation, Sunnyvale, Calif.

[21] Appl. No.: 75,260

[22] Filed: Sep. 13, 1979

Related U.S. Application Data

[63] Continuation-in-part of Ser. No. 17,575, Mar. 5, 1979, abandoned.

[51] Int. Cl.³ ...................... G01N 31/04; G01N 31/08
[52] U.S. Cl. ............................... 23/230 R; 210/198.2; 210/656; 210/662; 422/70
[58] Field of Search ........................ 23/230 R; 422/70; 210/25, 38, 31 C, 198 C, 198.2, 656, 662; 73/61.1 C

[56] References Cited

U.S. PATENT DOCUMENTS

| | | | |
|---|---|---|---|
| 2,617,766 | 11/1952 | Emmett et al. | 210/25 |
| 2,660,558 | 11/1953 | Juda | 210/685 |
| 3,849,306 | 11/1974 | Anderson | 210/685 |
| 3,897,213 | 7/1975 | Stevens et al. | 232/30 R |
| 3,920,397 | 11/1975 | Small | 422/70 |
| 3,920,398 | 11/1975 | Small et al. | 23/230 R |
| 3,923,460 | 12/1975 | Parrott et al. | 23/230 R |
| 3,925,019 | 12/1975 | Small et al. | 422/70 |
| 3,926,559 | 12/1975 | Stevens | 23/230 R |
| 4,036,751 | 7/1977 | Orita et al. | 210/662 |

Primary Examiner—Michael S. Marcus
Attorney, Agent, or Firm—Flehr, Hohbach, Test, Albritton & Herbert

[57] ABSTRACT

Apparatus and method for chromatographic separation and quantitation of different ions of like charges in a sample, e.g., cations or anions. Referring to anion separation, the sample is directed to a first chromatographic column of the ion exclusion type in which the weak acids (e.g., carboxylic acids) and their salts are partially or totally resolved and separated from a fraction of strong acids (e.g., mineral acids) due to Donnan exclusion. The resolved weak acids may be passed directly to a conductivity cell for quantitative detection. The strong acids may be directed to anion exchange bed with a highly ionized developing reagent and eluted in resolved form with the effluent being passed to a suppressor ion exchange bed wherein the developing reagent is converted to a weakly ionized form without destroying the anion separation. Then, a fraction of the strong acids is detected with the same or a different conductivity cell. Prior to separation, the strong acids are preferably directed through a concentrator column formed of ion exchange resin in which they are retained but not resolved while the remaining solution is removed. Thereafter, the developing agent used for separation of the strong anion is passed through the concentrator column to remove the anions for resolution. The same technique can be employed for cations. In an alternative mode, the system is employed to separate and quantitate weak acids but not the strong ones.

27 Claims, 7 Drawing Figures

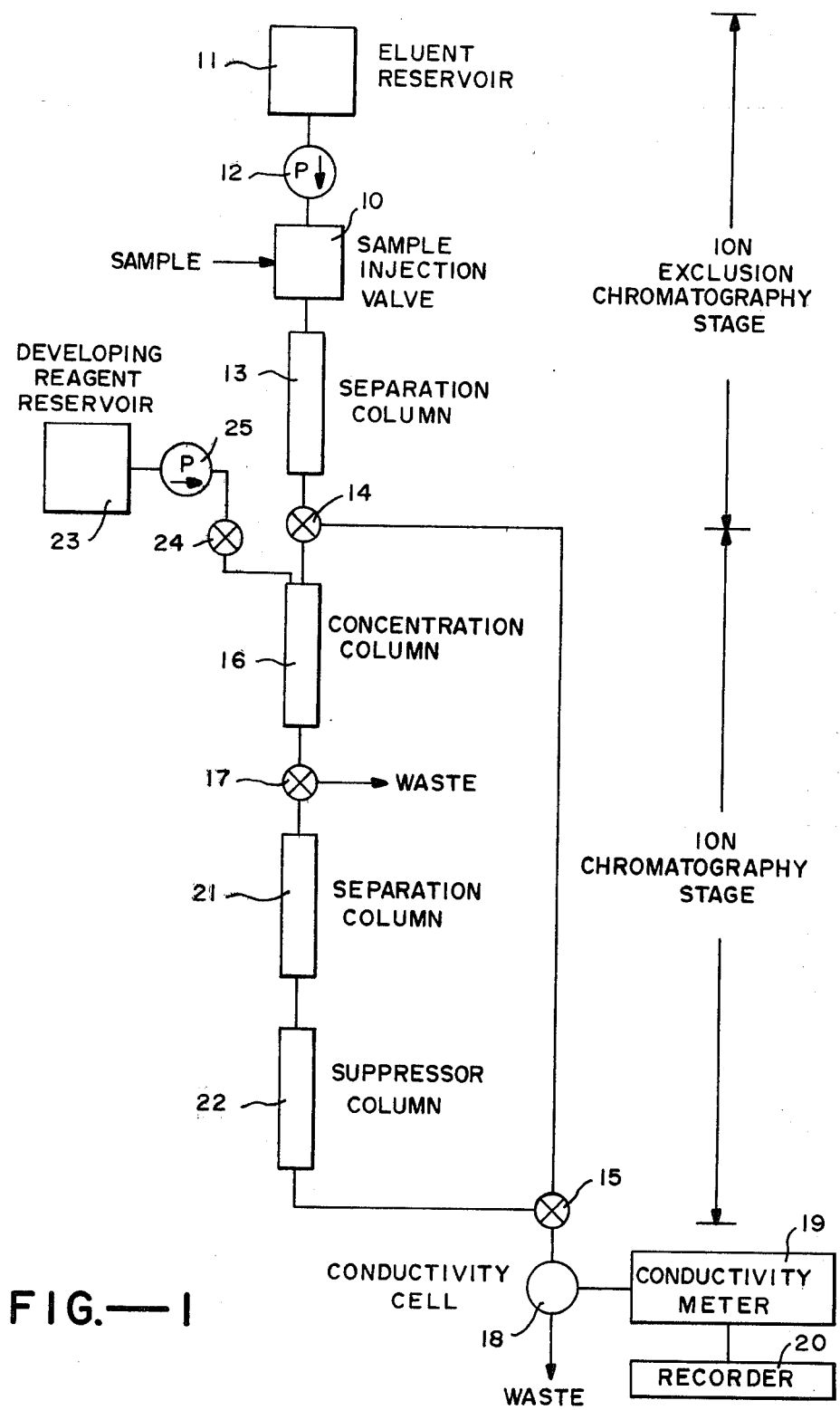
FIG.—1

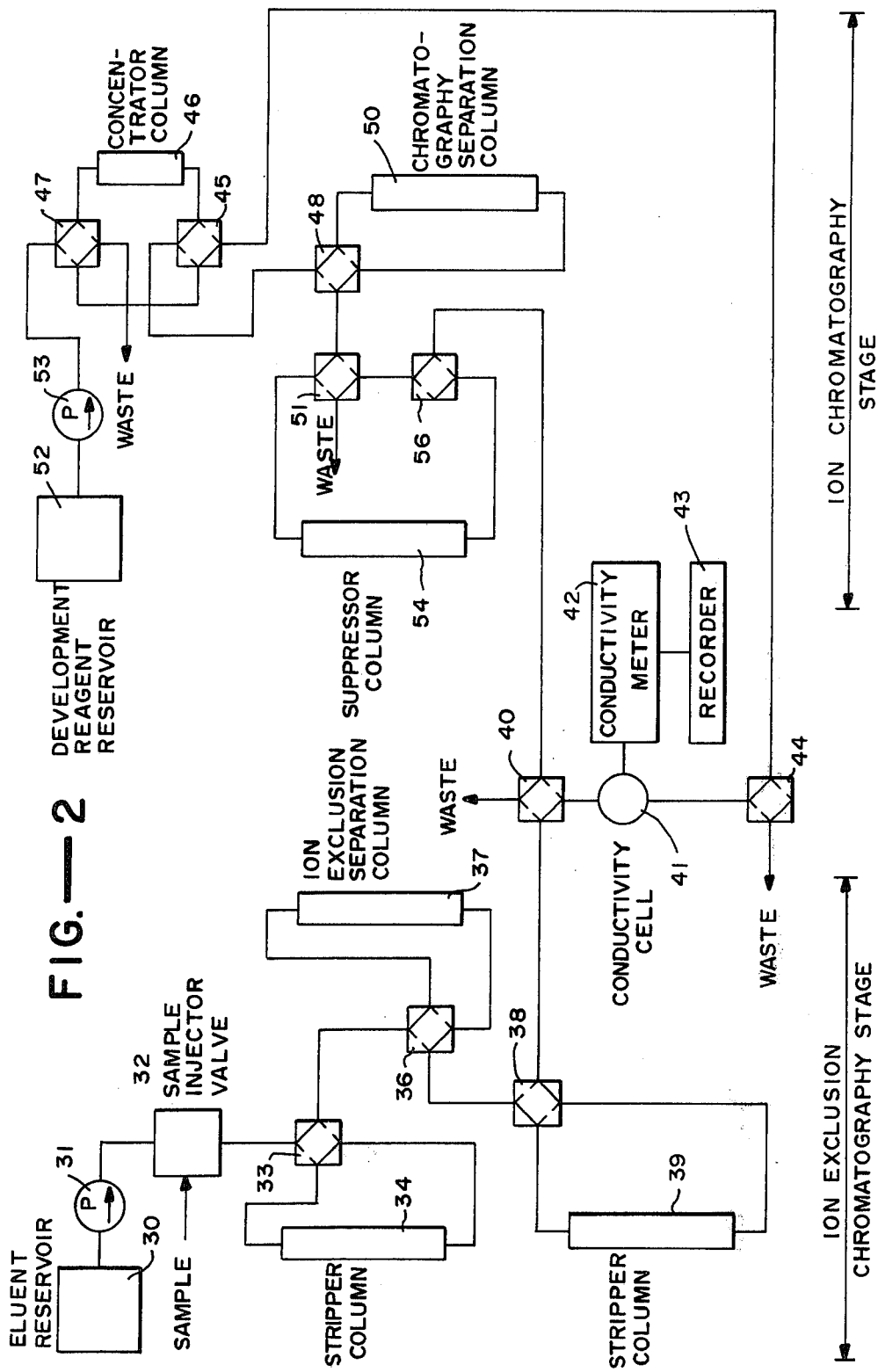
FIG.—2

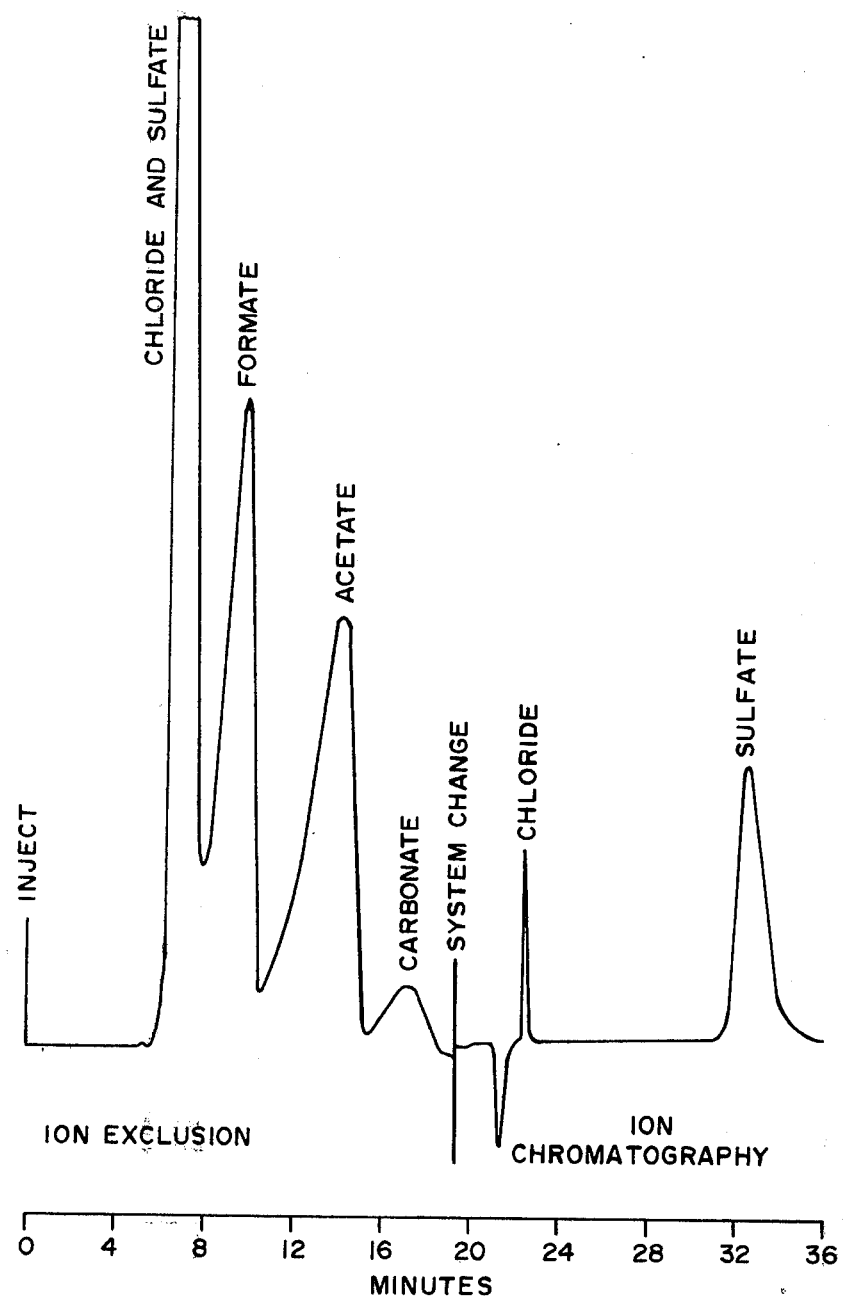
FIG.—3

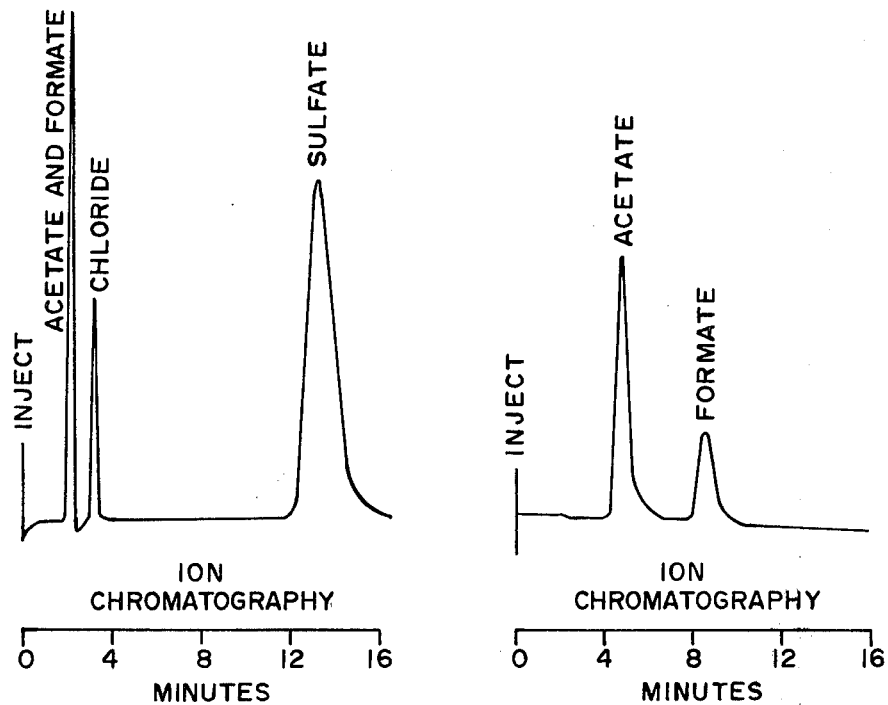
FIG.—4
FIG.—5
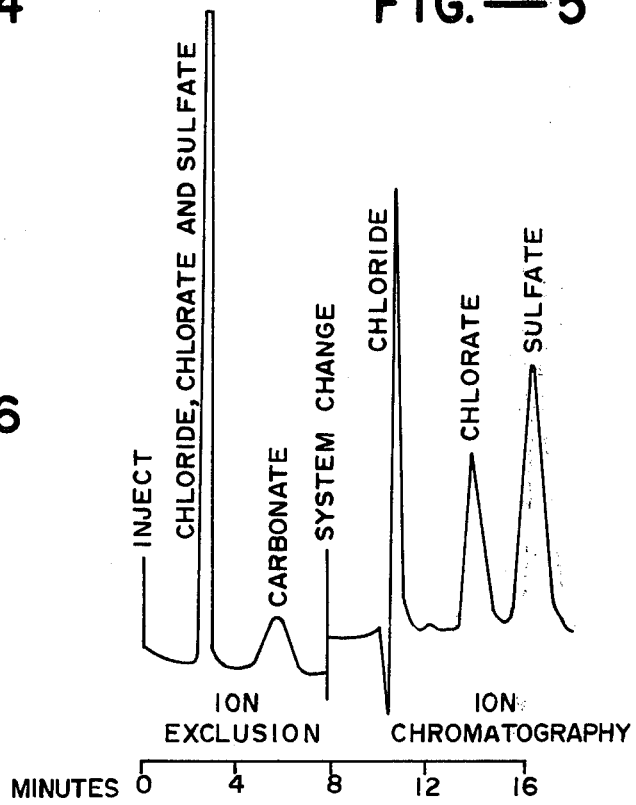
FIG.—6

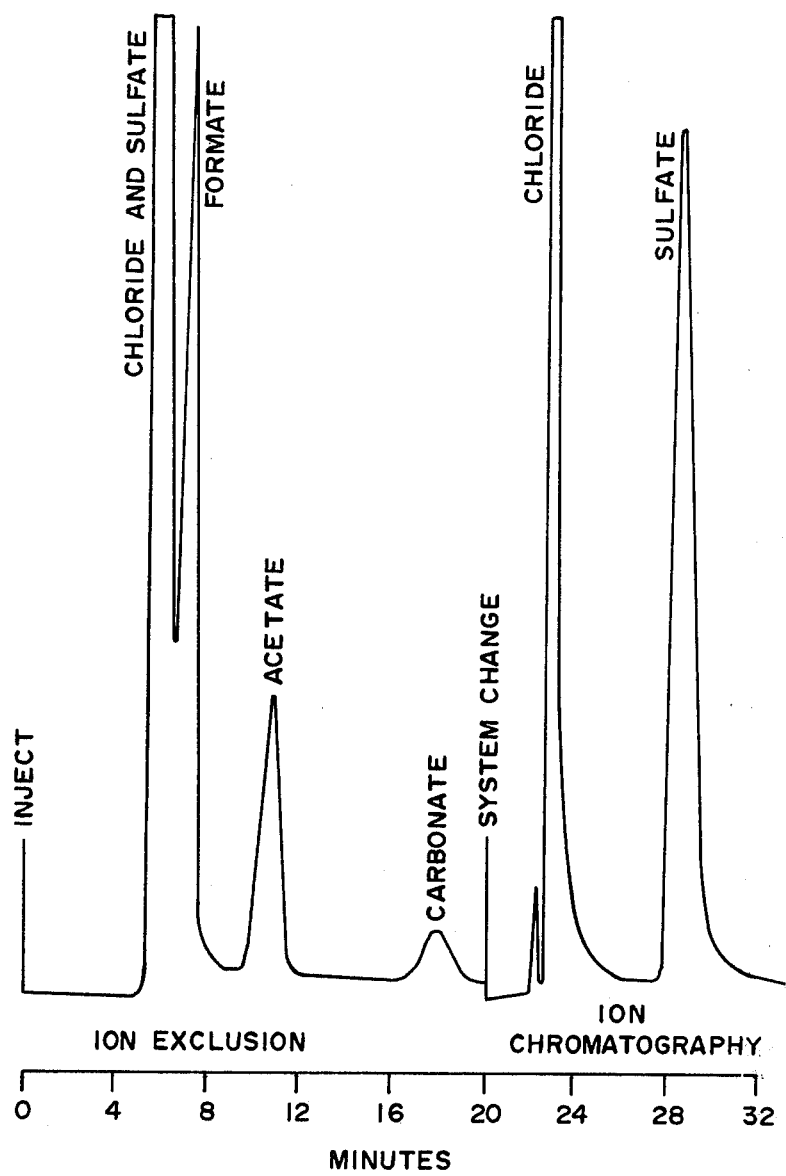
FIG.—7

COMBINATION APPARATUS AND METHOD FOR CHROMATOGRAPHIC SEPARATION AND QUANTITATIVE ANALYSIS OF MULTIPLE IONIC SPECIES

CROSS-REFERENCE TO RELATED APPLICATIONS

This application is a continuation-in-part of our co-pending patent application of the same title, Ser. No. 17,575 filed Mar. 5, 1979, now abandoned. Reference is also made to our copending patent application entitled "Method and Apparatus for Quantitative Analysis of Weakly Ionized Anions or Cations", Ser. No. 017,576 filed Mar. 5, 1979, now U.S. Pat. No. 4,242,097.

BACKGROUND OF THE INVENTION

The present invention relates to the quantitative analysis of a plurality of anions or cations in a single system.

The principle of ion exclusion chromatography with resins is known to be useful in separating strong acids or their salts as a class from weak acids or their salts. The theory of separation is that the resin network constitutes a semipermeable membrane from which highly ionized molecules such as mineral acids are excluded and pass through the column in the resin void volumn peak. While less ionized anions may be resolved by this technique and separated from the strong anions, the latter ions are not resolved from each other. The weak anions may be passed to a conductivity cell for quantitative detection providing water or other polar compounds are used as eluent.

Highly ionized ionic species have been resolved by ion exchange resin techniques and quantitatively detected as by use of a conductivity cell. A system of this type is set out in Small et al U.S. Pat. No. 3,920,397. However, the use of this technique is not capable of fully resolving a single sample containing strong and weak ionic species.

There is a need for the rapid analysis of the total ionic content of a sample stream which is rapid and accurate even at low concentrations.

SUMMARY OF THE INVENTION AND OBJECTS

It is an object of the invention to provide a technique for the total quantitative analysis of strong and/or weak cations or anions in a sample solution.

It is a further object of the invention to provide a technique capable of such analysis at very low levels such as for use in water monitoring in connection with pollution control.

Further objects and features of the invention will be apparent from the following description taken in conjunction with the appended drawings.

In accordance with the above objects, a method and apparatus for chromatographic quantitation of a number of ionic species in a solution of all positive or negative charge is provided which includes the combined techniques of ion exclusion and ion chromatography. Referring to the anion quantitation mode, the sample solution containing strong and weak acids is preferably directed through an ion exclusion resin column in the hydrogen form if water or other substantially ion-free solution is used as a developing reagent in which the strong acids or their salts are separated as a group in the resin void volume peak while the weak acids or their salts are resolved and subsequently eluted. The weak acids may be passed directly to a conductivity cell for quantitation.

The strong acids may be passed with developing reagent through an ion exchange resin bed for chromatographic separation and elution. Then, the solution of resolved strong acids is passed through another ion exchange resin bed in which the developing reagent is converted to a weakly ionized form or removed without disturbing the anion species separation and a stream is directed to a conductivity cell for quantitative detection. In another embodiment, certain of the weak anions are further resolved and quantitated but the strong anions are not resolved.

An ion concentration column is preferably disposed between the ion exclusion column and the ion chromatography column and is of a type which retains the ionic species without resolving them. It is of substantially lower capacity than the ion exclusion column and serves to remove the ionic species from the remainder of the solution. Then, the same developing agent used for ion chromatography is passed through the concentrator column and carries with it the ionic species for subsequent separation. If desired, multiple quantities of ionic species of choice may be collected on the concentrator column prior to separation and detection.

BRIEF DESCRIPTION OF THE DRAWINGS

FIG. 1 is a schematic representation of a simplified apparatus according to the present invention.

FIG. 2 is a schematic representation of a more detailed system in accordance with the invention.

FIG. 3 is a chromatogram illustrating the separation of strong and weak acids in accordance with the present technique.

FIG. 4 is a chromatogram illustrating the inability to separate the sample of FIG. 3 using ion chromatography alone.

FIG. 5 illustrates that the weak acids which could not be eluted by the chromatogram of FIG. 4 could be eluted using the system of the present invention.

FIG. 6 is a chromatogram of separation of anions in the presence of sodium hydroxide.

FIG. 7 is a chromatogram of the system of the present invention for the determination of anions in brine.

DETAILED DESCRIPTION OF THE PREFERRED EMBODIMENTS

The system of the present invention may be employed to determine a large number of strong and/or weak ionic species so long as the species to be determined are solely anions or cations. Such ionic species (e.g., anions) are normally associated with counterions but only ionic species of one charge type are determinable by the present method. Suitable samples include surface waters, including salt water, and other liquids such as industrial chemical waste streams, body fluids, such as serum and urine, and beverages such as fruit juices and wines. Covalent molecular compounds, such as amines, are often convertable to ionic form as by forming acid salts and thus analyzable by the present system.

Analysis is typically performed in an aqueous medium. However, it may be also performed in nonaqueous solvents provided the solvents are highly polar. Examples of suitable nonaqueous medium include the lower alcohols having from 1 to 4 carbon atoms and acetonitrile.

As defined herein, "weak anions" are anions which, in acid form, are ionized and have a relatively high $pK_A$ value (e.g., about 2 to 7) and which are resolved by ion exclusion chromatography in comparison to "strong anions" which are defined to be highly ionized in acid form, have a relatively low $pK_A$ value (e.g., 0 to about 2) and which are not resolved by ion exclusion chromatography.

As further defined herein, "weak cations" are cations which, in base form, are poorly ionized, have a relatively high $pK_B$ value (e.g., 2 to 7), and which are resolved by ion exclusion chromatography in comparison to "strong cations" which are defind to be highly ionized in base form, have a relatively low $pK_B$ value (e.g., 0 to about 2), and which are not resolved by ion exclusion chromatography.

As further defined, "weak ionic species" are either weak anions if the method is used for their separation or weak cations if the system is used for their separation; while "strong ionic species" are defined in an analogous manner.

Typical weak anions include mono-, di- and tricarboxylate groups (e.g., formates and acetates), carbonates, alkyl sulfonic acid, phosphonic acids, and phosphoric acids.

Typical strong anions include strong mineral acids, and specifically include halides, sulfate, chlorate, nitrate. Typical weak cations include primary, secondary, and tertiary amines, and ammonia.

Typical strong cations include alkali metals, and alkaline earth metals.

While the present technique may be employed to quantitatively analyze anions or cations, unless otherwise specified, the present application will refer to anions as the ionic species to be analyzed.

A simplified apparatus for performing the method of the present invention is illustrated in FIG. 1. Sample is supplied to the system suitably by a syringe (not shown) at sample injection valve 10. The sample is carried through the system by eluent drawn from reservoir 11 by pump 12 which thereafter passes into chromatographic separation column 13 of the ion exclusion type to be described below. The first effluent from the column includes strong anions which pass as a fraction through column 13 in the void volume peak and are directed by valve 14 in unresolved form to a concentrator column 16 which includes an ion exchange resin of relatively low capacity to retain the ionic species in the fraction. After the strong anion fraction passes valve 14, flow is terminated to concentrator column 16. The effluent from concentrator column 16 is directed by valve 17 to waste and includes the solution associated with the retained strong anions.

After elution of the strong anions, from separation column 13, the chromatographically resolved weak anions are eluted. They are passed through valve 15 in a position to flow them through a liquid conduit to conductivity cell 18. The electrical signal emitted at cell 18, in which the fluctuation in ionic concentration produce an electrical signal proportional to that amount of ionic material and registered by conductivity meter 19, is directed to recorder 20 which provides a visible readout. The conductivity meter 19 and recorder 20 together constitute a readout for the signal from conductivity cell 18. After passing through the conductivity cell, the liquid is passed to waste.

Separation of the weak anions by means of separation column 13 is designated in the drawing as "ion exclusion". The principles of this technique are described below. The other portion of the system to be described below is designated in the drawing as "ion chromatography". In the latter procedure the strong anions are resolved and, if desired, weak anions are further resolved.

Ion chromatography is defined herein to refer to resolution of ionic species on ion exchange resin on the basis of the difference in strengths of their charges.

Referring to the ion chromatography section of the system, after retention of the strong anions on the concentrator column, valve 17 is switched to direct subsequent fluid to a second chromatographic separation column 21 and then via a conduit through chromatographic suppressor column 22.

Developing reagent from reservoir 23 is passed through a valve 24 drawn by pump 25 into concentrator column 16 and carries with it the ions retained on the resin therein for passage through valve 17 into separation column 21 in which the strong anions are resolved. The solution leaving column 21 with the resolved strong anions is conveyed by a liquid conduit to suppressor column 22 in which the developing agent either is retained at ion exchange sites or converted to weakly or substantially non-ionized molecular form.

Then, after completion of the foregoing quantitation of the weak anions from column 13, valve 15 is switched to pass the resolved species from column 22 to a liquid conduit to common conductivity cell 18. The electrical signal of the conductivity meter is directed to recorder 20.

In performing the present method, the sample size is preferably small to facilitate rapid sharp separations and determination. Also, this avoids overloading of low capacity separator column 21 so that it is not necessary to employ large volumes of developing reagent which must be stripped in suppressor column 22. Suitable samples are on the order of 0.002 to about 5 ml of a dilute solution containing the ionic species, typically not greater than about 1 to 10% of the ion exchange capacity of separator column 21.

It is preferable to use a pump both for eluent from reservoir 11 and developing reagent from reservoir 23 to sweep the sample through the respective portions of the systems. Typical flow rates fall generally in the range from about 46 to 460 ml/hour of solution of eluent from reservoir 11 and developing reagent from reservoir 23.

The sample to be analyzed include ionic species of common positive or negative charges. One particular anion application is the determination of chloride, chlorate, sulfate and carbonate in a highly concentrated sodium hydroxide solution. Another is the determination of trace sulfate, acetate and formate in sodium chloride (brine) solutions. Both determinations employ relatively low operating pressures, have low detection limits, and are rapid. This is of particular benefit in the chlor-alkali industry.

The technique of separation in column 13, is known as ion exclusion chromatography. The accepted theory of separation is that the resin network serves as a boundary, which behaves as a semipermeable membrane, between the interstitial liquid between the resin particles and the occluded liquid inside the resin. Due to Donnan exclusion, highly ionized molecules, such as strong mineral acids, are excluded from the resin particles and passed directly through the column in the void volumn peak. Weakly ionic molecules, such as many carboxylic or other organic acids and their salts (e.g., acetate and formate), may enter the resin phase in acid form and are retained by the resin for later elution than strong acids. Other weak acids include carbonic acid and hydrogen sulfide. Weak acids and their salts are readily separated from strong acids and their salts on separation column 13 in this manner.

The sample may be passed over column 13 charged with a cation exchange resin in the hydrogen ion form using an aqueous solution with low specific conductivity (e.g., water) as the eluent. In special applications, alcohol may also be used as the eluent. Salts of weak acids are converted on the resin to their free acid form, and any metal hydroxide present are neutralized by ion exchange action. Separation of the weak acids from the strong acids or their salts occurs as the sample moves through the resin bed in accordance with the foregoing principles.

Chromatographic separation by ion exclusion is principally due to the distribution coefficient $K_d$, which equals $C_r/C$. $C_r$ is the concentration of the solute in the liquid phase inside the resin and $C$ is the concentration of solute in the liquid phase outside the resin particles. Separation depends upon factors which effect $K_d$ such as $pK_A$, concentration of the solute and characteristics of the resins such as cross-linkage and ion exchange functionality. Generally, the $pK_A$ can be used to predict elution order but van der Waals forces can become dominant if the number of aliphatic or aromatic carbons become large as with fatty acids. Altering the pH level of the eluent has a pronounced effect upon the separation of weak acids because the degree of ionization changes with pH.

In general, the weak acids in their molecular unionized form can penetrate into the interior of the ion exchange resin while the strong highly ionized acids are excluded. By using ion exchange resin in hydrogen ion form, salts of weak acids which are highly ionized (e.g., of alkali metals) are converted to their acid form which may be retained by the column. For example, sodium acetate is converted on the column to acetic acid and the sodium ion is retained by the column. Thereafter, the acetic acid is resolved from other weak acids and eluted from the column in a separate peak volume which can be detected. The above discussion of ion exclusion chromatography applies in an analogous manner to the separation of cations, except, in this case, an anion exchange resin in the hydroxide form is used in the ion exclusion column.

The resin employed in ion exclusion column 13 is of a type in which the dominant retentive force is penetration of the weak acid in molecular form into the interior of the resin for retention there for a time until elution in the eluent stream in inverse order to such retention forces. This effect dominates over any ion exchange effect. To permit this to occur, the pore size of the resin should be relatively large to permit penetration of such molecules. A suitable substrate of this type is a surface sulfonated copolymer of styrene and divinylbenzene having about 1 to 8% divinylbenzene cross-linking. Suitable ion exchange groups for anion analysis include sulfonate and for cation analysis include trimethylammonium or similar quarternary ammonium tupe resins. Suitable sizes for the particles are on the order of 200 to 400 mesh (U.S. sieve series) although finer sizes may be used if desired. The specific exchange capacity of the resin particles is not critical. A suitable level is on the order of about 0.1 to 5 milliequivalent per gram (m.eq./g.) of resin.

As set out above, the ion exclusion resin for anion separation is preferably in the hydrogen ion form. This permits conversion of the weak acids to their unionized molecular form. In addition, it causes stripping of cations which could provide interference background in conductivity cell 18. However, if desired for specialty applications, non-ionic resin may be employed, so long as the counterions in the sample are preconverted to acid form for the separation of anions or base form for the separation of cations. This is preferably performed by using a strong acid or strong base eluent. Suitable non-ionic resins are so-called silica based reverse phase resins. Specific suitable ones are sold under the trade designation μ-BondaPak C-18 by Waters Associates.

The separation column 21 and suppressor column 22 herein may be of the same type as described with respect to separator 10 and stripper 11 of FIG. 1 in Small et al U.S. Pat. No. 3,920,297, incorporated at this point by reference. Briefly, the ion exchange resin for separator column 21 is preferably of high performance in its ability to separate ionic species but at the same is of low specific capacity so that only a small concentration of developing reagent is required to accomplish separation and elution from the resin bed. Suitably, the specific exchange capacity may be in the range of about 0.005 to 0.1 m.eq./g. of resin. For high performance, highly active ion exchange sites are preferably disposed at a surface layer of the resin beads or particles. The preferred separator resin is pellicular in nature with the active sites at or close to the surface of the resin beads. Less preferred are more highly cross-linked ion exchange resins which are porous having active sites along the walls of the pores with the pores providing more accessability to the ionic species than in gel-type resins. Suitable resins are described in the last-named U.S. patent.

Suppressor column 22 is analogous in function to stripper column 11 of FIG. 1 in the last-named U.S. Pat. No. 3,920,297. The principles of operation of that column, its detailed description, and its relationship in functional characteristics with respect to the separation column are incorporated by reference at this point. This column is of a relatively high specific capacity in comparison to separator column 21. This is because the function of this suppressor column is to preclude passage of the developing reagent in highly ionized form while permitting passage of the ionic species resolved on separation column 21 without substantial interruption. Suitable ion exchange resins for analysis of anions are polystyrene or modified polystyrene cross-linked with divinylbenzene carrying nuclear groups, the latter provide a reactive exchange sites. The strong cation exchange resins include nuclear sulfonic acid or sulfonate groups along the polymer chains while the weak cation exchange resins carry carboxylate groups. The strong base anion exchange resins carry nuclear chloromethyl groups which have been quarternized. The weak base exchange resins carry nuclear primary, second or tertiary amine groups.

The nature of the resin in suppressor column 22 is determined by the developing reagent to be suppressed. A common developing reagent in anion analysis is sodium carbonate or sodium bicarbonate in an aqueous form. For this reagent, a suitable resin is highly cross-linked polystyrene including sulfonic groups in the hydrogen ion form. The high cross-linking assures that ion exchange effects predominant over chromatographic penetration into the resin. The sodium ion is stripped from the developing reagent to form weakly ionized carbonic acid which elutes from the column in substantially unionized molecular form and so which does not interfere with detection in the conductivity cell.

As set out above, the combination of separation column 21 and suppressor column 22 is analogous to the corresponding system of U.S. Pat. No. 3,920,397. Similarly, analagous modifications are made to the operating conditions, eluents, and resin types for conversion from anion analysis to cation analysis.

Concentrator column 16 may contain ion exchange resin of the same type as separator column 21. Its function is to retain only ionic species while passing the remainder of the solute to waste, but to rapidly release such ionic species in the presence of developing reagent from reservoir 23 for flow and resolution in separation column 21. Thus, in the anion system, the concentrator column may be used to collect the strong acid void volume peak before injection into separator column 21. The amount of capacity of resin in the concentrator column is sufficient for retention but not resolution of the ionic species. By way of comparison, concentrator column 16 should have from 2 to 20 times the total ion exchange capacity compared to the ion concentration of the peak to be collected. Another comparison is that separation column 21 should have at least 10 times the ion exchange capacity of concentrator column 16. While the same type of resin at different capacity can be used for the two columns, other types of resin may also be employed so long as the same functional characteristics are obtained.

FIG. 2 illustrates a more detailed schematic representation of apparatus suitable for the present invention. Eluent from reservoir 30 is pumped via pump 31 to carry sample injected in sample injection valve 32 to valve 33. In a first position of valve 33, the solution is directed through stripper column 34 including ion exchange resin of a type which strips predetermined interfering ionic species prior to passage to the ion exclusion separator column. After passage through the stripper column, the solution goes back through valve 33 and in through a fluid conduit into valve 36. In an alternative second position of valve 33, stripper column 34 is bypassed.

In a first position of valve 36, fluid is directed through a conduit through ion exclusion separation column 37 of the same type as column 13 of FIG. 1 and then back through valve 36 to valve 38. In a second position of valve 36, the solution bypasses column 37 and proceeds directly to valve 38.

Valve 38 includes a first position in which fluid passes through a stripper column 39 and back through valve 38 to valve 40. Stripper column 39 is employed where the eluent includes a strong acid for the analysis of anions or strong base for the analysis of cations to facilitate chromatographic separation on the ion exclusion column and the stripper column is of a type which removes the anion of the acid or the cation of the base. For example, for hydrochloric acid as the eluent, the stripper column may be a cation exchange resin in the silver ion form while for barium hydroxide as the strong base, the stripper column may be an anion exchange resin in the sulfate form. It is apparent that stripper column 34 would not be employed as a prestripper if it would be of a type to strip the strong acid or strong base eluent. Thus, typically, columns 34 and 39 are not used in combination.

Valve 40 includes a first position in which the solution from valve 38 is directed through conductivity cell 41 which is provided with readout means consisting of conductivity meter 42 and recorder 43. Thereafter, the solution passes through valve 44 to waste. In this position of valve 40, those ions resolved in column 37 may be analyzed.

As illustrated in FIG. 2, the above described portion of the system is employed for the ion exclusion chromatography stage. The remainder of the apparatus employed for the ion chromatography stage is now described.

In a second position of valve 44, the solution which has passed through the conductivity cell passes to valve 45. In a first position of that valve, the liquid passes through concentrator column 46 wherein the ionic species to be analyzed are retained and the remainder of the solution passes into valve 47 and to waste. In a second position of valve 45, the solution bypasses concentrator column 46 and flows to valves 47 and to waste.

Eluent for ion chromatography is directed from reservoir 52 under pressure supplied by pump 53 through valve 47 which in a second position permits it to flow through concentrator column 46 to remove the retained ionic species and pass through valve 45 and 48 and downwardly through ion chromatography column 50 and back to valve 48 and valve 51 which in a second position passes solution to suppressor column 54 and to valve 56. There, the solution flow through the fluid conduit to valve 40. At the latter valve, the solution again may be either passed to waste or into conductivity cell 41 and through valve 44 to waste.

SEQUENCE OF OPERATION OF FIG. 2

The following description will refer to one sequence of operation of the system of FIG. 1. For simplicity of description, flow of solutions will be described in order of flow without reference to valve settings. The valves will be assumed to allow flow in the described manner. In the first described system, a water eluent is utilized in reservoir 30.

In the first step, the system is equilibrated. In the ion exclusion section, water from reservoir 30 is pumped via pump 31 to bypass sample injection valve 32 and flow through valves 33 and 36 downwardly through ion exclusion column 37, back through valve 36 into valve 38 to valve 40 and through conductivity cell 41 and valve 44 to waste. At the same time, developing reagent from reservoir 52 equilibrates the ion chromatography stage. It passes through pump 53 and valve 47 bypassing concentrator column 46 to valve 45 through valve 48 and downwardly through column 50, back through valve 48 and through valve 51 to pass downwardly through suppressor column 54 and through valves 56 and 40 to waste.

In the next step, sample is injected into injection valve 32. Eluent from reservoir 30 is passed through the sample injection valve to carry sample to valve 33. If desired, the sample may be passed through prestripper column 34.

Thus, for example, in the presence of a high concentration of metal halides such as sodium chloride or hydrogen halides such as hydrochloric acid, the halides may be removed by passing the sample through a column charged with a cation exchange resin in the silver form. This will be described further below.

Whether or not a sample goes through stripper column 34, it is passed through valve 36 and onto ion exclusion separation column 37. There, the strong anions pass through the column in the void volume peak and are carried through valves 36, 38 and 40 to conductivity cell 41. There, the conductivity meter 42 takes a continuous reading registered by recorder 43. Since the strong acids are not resolved, this reading is not sufficient, and the solution is passed through valves 44 and 45 and into concentrator column 46. The strong anions are retained on the concentrator column while the remaining solution passes through valve 47 to waste. During this time, developing reagent from reservoir 52 is continuously equilibrating the rest of the ion chromatography section as set out above.

In the next step, the weak anions which are resolved on separation column 37 are eluted through the conductivity cell 41 and analyzed. After the stong anions have passed through valve 44, and before the resolved weak anions from column 37 are passed through the same, valve 44 is switched to waste. The resolved weak anions which pass through conductivity cell 41 are detected by conductivity meter 42 and visibly displayed by recorder 43.

In the next stage, after complete resolution of the weak anions valve 40 is switched so that flow through the ion exclusion column 37 passes to waste. Then, the developing reagent from reservoir 52 is drawn by pump 53 through valve 47 to pass downwardly through concentrator column 46 and to carry the strong anions contained therein through valves 45 and 48 to pass downwardly through ion chromatography separation column 50 wherein the anions are resolved. The resolved anions are then passed through valve 48 and valve 51 downwardly through suppressor column 54 which includes an ion exchange resin of a type which substantially precludes passage of the developing agent in highly ionized form but which permits passage of the resolved ionic species. The function of this column is the same as set forth above with respect to suppressor column 22 of FIG. 1.

The output from suppressor column 54 is directed through valve 56 and valve 40 and through conductivity cell 41 and valve 44 to waste. The electrical signal from the conductivity cell 41 is directed to the conductivity meter and the output is directed to recorder 20 as set out above.

By use of the above system, a continuous recording may be made during the entire cycle. By way of example, a mixture of strong acid anions such as nitrate and sulfate with a weak acid anion such as carbonate would be resolved as follows. The first volume or fraction of sample through conductivity cell 41 containing the strong acids in the void volume peak would be recorded as a single peak of nitrate and sulfate. Then, the weak acids would pass through the conductivity cell in resolved form and be recorded. Thereafter, the strong anions which have been resolved in the ion chromatographic stage would pass through the conductivity cell and be recorded in resolved form.

In another embodiment, the eluent from reservoir 30 would include a strong acid (e.g., HCl) developing reagent for anion resolution (or base for cation resolution) to assist ion exclusion separation in column 37. As the purpose of such developing reagent is to assist separation on column 37, a prestripper column 34 would not be used as it would strip the developing reagent acid.

By use of a strong acid or base as the eluent for passage through column 37, it would be necessary to strip the strong anion or cation, respectively, from the solution prior to passage through the conductivity cell. Otherwise, this would provide an unacceptable high background for detection. For this purpose, the elution exiting from column 37 is passed through stripper column 39 by appropriate adjustment of valve 38. The stripper column may be of the same type described above with respect to stripper column 34. Thus, for hydrochloric acid eluent, a cation exchange resin in the silver ion form may be employed. Conversely, for a system for analyzing cations and using barium hydroxide as the eluent, an anion exchange resin in the sulfate form may be employed.

A system of the foregoing type which combined ion exclusion separation chromatography with a strong acid or base eluent followed by stripping of such eluent is described in our aforementioned co-pending application entitled "Method and Apparatus for Quantitative Analysis of Weakly Ionized Anions or Cations", Ser. No. 017,576 filed Mar. 5, 1979. Briefly, the strong acid or base suppresses ionization of the weak anions or cations by converting them to acids or bases and thus improves chromatographic resolution on an ion exclusion column.

Prestripper column 34 is particularly useful when the sample is an aqueous solution of weak and strong acids (or bases) or their salts in the presence of large amounts of ionic species which could interfere with trace analysis of other acids or salts present in the mixture. Such species are thus removed by passing the sample through stripper column 34. Thus, for example, the halide anions of metal halides such as sodium chloride or hydrogen halides such as hydrochloric acid may be readily removed by passing the sample through the aforementioned column charged with a cation exchange resin in the silver form. As the sample passes down through the column, the metal or hydrogen ion exchanges for silver ion and the free silver ion precipitates the halide (chloride) in situ. Similarly, if large quantities of sulfuric acid or metal sulfates are present in the sample, the sample may be passed through a column charged with a cation exchange resin in the barium form. The metal or hydrogen ion in the sample exchanges for barium ion and the free barium ion precipitates the sulfate in situ. Of course, under these circumstances, the ions removed from the system cannot be analyzed.

It is apparent that the foregoing system is particularly useful for the total analysis of a plurality of ionic species in a sample solution of the same charge. Thus, it permits an automated continuous process for the rapid detection and analysis of both strong and weak ionic species of the same charge. Groups of ions which can not be analyzed by ion exclusion chromatography or ion chromatography alone may be analyzed in a continuous rapid quantitative analysis at high sensitivity and resolution.

The use of a concentrator column in the present system increases its versatility. Thus, it permits the concentration of ionic species in the absence of its accompanying solution so that upon removal with the developing reagent, there is a minimum disturbance of the equilibrium of the separation column. In addition, if desired, multiple injections of the same sample may be made to supply multiple quantities of ionic species on the concentrator column to be resolved as a composite sample on ion chromatography column 53. This is particularly useful for trace quantities of an ionic species which may be difficult to resolve using a single sample. Also, by use of multiple concentrator columns (not shown) and/or appropriate adjustment of the valving, it is possible to resolve predetermined highly specific peaks by repeated runs of preselected ionic species. Thus, although the system has been described in terms of using ion chromatography to resolve only the strong acids or bases which pass through the void volume peak by the ion chromatography stage, it should be understood that the weak ionic species which are at least partially resolved during ion exclusion on column 37 may be further resolved by ion chromatography in column 50. This may be done by loading such ionic species on the illustrated single concentrator column or by the use of multiple concentrator columns (not shown) in parallel and by appropriate adjustment in the valving. Thus, since ion exclusion and ion chromatography resolve the ionic species by different mechanisms, it may be possible that two weak acid or base ionic species may be difficult to fully resolve by ion exclusion alone but may be fully resolved by a combination of ion exclusion chromatography on separation column 37 and ion chromatography on separation column 53. One or more concentrator columns 49 facilitate this viewing or preselected peaks of ionic species.

In certain instances, the present system can be employed for the separation of and quantitation of weak ionic species without quantitation of the strong ionic species. Here, referring to FIG. 2, the first separation column 37 in FIG. 1 would serve to perform a preliminary or partial separation of the weak ionic species from each other and to exclude or separate the strong ionic species as a group from the weak ionic species. Some or all of the weak ionic species would be further resolved by ion chromatography in column 50 as described in the previous paragraph. The difference is that the strong ionic species may be passed to waste as a group without resolution or quantitation. In addition, if desired, any fraction of weak ionic species eluting from valves 36 and 38 may be also passed directly to conductivity cell 41 for quantitation.

Fig. 2 illustrates one embodiment of the present invention. It should be understood that variations can be made without departing from the intended scope. For example, additional or different conduit paths may be provided for improved or analogous purposes. Thus, in an embodiment not shown, independent conductivity cells may be used for simultaneous detection of effluent from the ion exclusion and ion chromatography stage for more rapid analysis. Also, if desired, it may be possible to pass part of the sample stream directly from the ion exclusion stage to the ion chromatography stage without first passing through a conductivity cell.

A further disclosure of the nature of the present invention is provided by the following specific examples of the practice of the invention. It should be understood that the data disclosed serve only as examples and are not intended to limit the scope of the invention.

EXAMPLE 1

The following sample is used—sodium formate 25 ppm; sodium acetate 75 ppm; sodium carbonate 100 ppm; sodium chloride 4 ppm; sodium sulfate 50 ppm. The general system of FIG. 2 was employed. The sample is injected through a sample injection valve equipped with a 100 microliter sample loop. The sample is eluted by a pumped stream of deionized water at 69 ml per hour.

The first effluent from column 37 containing the strong anions (chloride and sulfate) in the void volume peak is directed through the conductivity cell through concentration column 46.

After such strong acids are eluted from column 37, before the weak acids began to elute, the effluent is directed to waste. The weak acids resolved on column 37, are passed through conductivity cell 41 and the electric signal of the ionic species is recorded.

The valve 44 is actuated and development reagent (3 mM $NaHCO_3$ and 2.4 mM $Na_2CO_3$ in an aqueous solution) is passed through concentrator column 46 at a rate of 140 ml/hour. Columns 50 and 54 are preequilibrated with the carbonate buffer solution. The effluent is directed to separation column 50. Then, the effluent is passed to suppressor or column 54 in which the sodium ion of the developing reagent is removed to suppress ionization of the carbonate. The effluent from suppressor column 54 is directed through conductivity cell 41 and recorded.

The chart recorder output is shown in the chromatogram of FIG. 3. All five species present are separated in 36 minutes. (Use of a 3×150 mM separator column would reduce the analysis time to 24 minutes without interference.)

Referring to the chromatogram of FIG. 3, the first four peaks comprise the detection in the conductivity cell of the anions which pass only through ion exclusion column 37.

The resin columns were of the following type:

(a) ion exclusion column 37—a 6×500 mm column filled with a strong acid cation exchange resin in the hydrogen ion form at 200 to 400 mesh size, sold under trade designation "Dowex 50W-X4 Resin" by the Dow Chemical Company.

(b) concentrator column 46—a 3×50 mm column filled with low capacity pellicular anion exchange resin in the bicarbonate form to trap the strong anions. The specific resin employed is of the quarternary ammonium type having an ion exchange capacity of about 0.02 m.eq./g. This resin is a surface sulfonated styrene divinylbenzene copolymer and treated with a quarternary ammonium form latex, the latex resin having particle sizes mainly in the range of about 0.1–1 microns major dimension as measured dry. This product is sold in packed columns designated as anion concentrator columns by Dionex Corporation. It is a low capacity column.

(c) ion chromatography column 50—a 3×500 mm column including the same type capacity resin as concentrator column 46.

(d) suppressor column 54—a 6×250 mm column of high capacity cation exchange resin in the hydrogen form sold under the trade designation Dowex 50W-X16 by Dow Chemical Company.

The strong acid peaks of chloride and sulfate are unresolved by ion exclusion alone. However, the weak acid peaks of formate, acetate and carbonate are resolved. In the second part of the chromatogram, chloride and sulfate peaks are illustrated after passing through the ion chromatography stage of the system. It is apparent that these ions are fully resolved by ion chromatography once they are removed from the weak anions (formate, acetate and carbonate).

EXAMPLE 2

This is a comparative example to illustrate the advantage of using combined ion chromatography with ion exclusion. The same sample is injected into the same apparatus except that ion exclusion column 37 was bypassed. The sample is eluted from the ion chromatography stage in the same manner as set out above. The chromatogram of FIG. 4 illustrates that acetate and formate are unresolved by ion chromatography and carbonate is undetected. The analysis time is 16 minutes.

EXAMPLE 3

In another comparative example, the same system as in FIG. 2 is employed except that a different eluent of 2.5 mM sodium borate was employed. The chromatogram shown in FIG. 5 illustrates that formate and acetate may be resolved by the system. However, chloride and sulfate did not elute from separator column 50 and carbonate remained undetected. Analysis time including equilibrium for this detection is approximately 70 minutes.

EXAMPLE 4

Another comparative experiment, 10 microliters (ml) of 4% sodium hydroxide containing 10 ppm chloride, 50 ppm chlorate, 50 ppm sulfate and 75 ppm carbonate is injected to the system of Example 1. In this experiment, ion exclusion column 37 is a 6×500 mm column of strong acid cation exchange type resin in the hydrogen ion form sold under the trade designation Dowex 50W-X16 by Dow Chemical Company. Here, the eluent is de-ionized water. The ion chromatographic system and conditions are the same as described in Example 1 except the eluent flow rate is 92 ml/m.

The results are shown in the chromatogram of FIG. 6. The strong anions (chloride, chlorate and sulfate) are eluted as a single peak during ion exclusion and are fully resolved during ion chromatography. Thus, it is apparent that the sodium hydroxide is essentially removed from the system on ion exclusion column 37 and does not interfere with the chromatogram.

EXAMPLE 5

This example uses the same conditions as the preceding one with the exception that a silver stripper column 34 was placed on stream to remove excess chloride ions from the matrix. In this instance, 50 ppm sulfate and 10 ppm formate, 10 ppm acetate is analyzed in 2.5% sodium chloride. The silver stripper column is a 3×150 mm column filled with strong acid cation exchange type resin in the silver form sold under the trade designation Dowex 50W-X16 by Dow Chemical Company. The chromatogram is illustrated in FIG. 7.

It is apparent that by use of the silver stripper column, a rapid and interference free analysis is provided for determining both weak and strong acids or their salts in a single chromatographic procedure even in the presence of brine (sodium chloride) solutions. The sodium chloride is stripped from solution on the silver stripper column.

What is claimed is:

1. The method of chromatographic separation and quantitative analysis of a plurality of anionic species in a sample solution, said method comprising
   (a) directing a sample solution containing a plurality of anionic species and an eluent through a first resin column, said first column containing a cationic or non-ionic chromatographic resin in a form to substantially resolve at least a first weak anionic species member, having a $pK_A$ value of about 2 to 7, from a group of anionic species including at least first and second strong anionic species members, having $pK_A$ values of about 0 to 2, on elution from said column in said eluent,
   (b) directing a solution of at least said substantially resolved first weak anionic species through a conductivity cell having associated readout means and measuring the conductivity of said last named solution,
   (c) directing the first and second strong anionic species and a highly ionized developing reagent solution through a second resin column, said second resin column containing a chromatographic anion exchange resin in a form to substantially resolve at least said first and second strong anionic species on elution from said second column,
   (d) directing said substantially resolved first and second strong anionic species to a third resin column, said third resin column containing a cation exchange resin of a type which substantially precludes passage of the developing reagent in highly ionized form and which permits passage of said resolved first and second strong anionic species without substantiall interruption of the resolution, and
   (e) directing a solution of the resolved first and second strong anionic species from said third resin column through a conductivity cell having associated readout means and measuring the conductivity of said last named solution.

2. The method fo claim 1 in which said sample solution includes at least a second weak anionic species.

3. The method of claim 2 together with the steps of:
   (f) separating said second weak anionic species together with said first weak anionic species from first and second strong anionic species in step (a),
   (g) directing said at least first and second weak anionic species and a highly ionized developing reagent through a resin column containing a chromatographic anion exchange resin in a form to substantially resolve said first and second weak anionic species,
   (h) directing said substantially resolved first and second weak anionic species to a cation exchange resin column of a type which substantially precludes passage of the developing reagent in highly ionized form and which permits passage of said resolved first and second weak anionic species without substantial interruption of the resolution, and
   (i) directing a solution of the resolved first and second weak anionic species through a conductivity cell having associated readout means and measuring the conductivity of said last named solution.

4. The method of claim 3 in which prior to step (g), the first and second weak anionic species are directed through an ion concentrator column including an anion exchange resin on which the anionic species are retained without substantial resolution while the unretained solution associated with said anionic species pass through the concentrator column and is removed, and then the developing reagent is passed through said concentrator column to remove said first and second weak anionic species and carry them to the chromatographic column of step (g) for performance of that step.

5. The method of claim 2 in which said first chromatographic column resin is in a form to substantially resolve said first and second weak anionic species, and a solution of said resolved first and second weak species is passed through a conductivity cell having associated readout means and the conductivity of the last named solution is measured.

6. The method of claim 1 in which the resin in the first resin column is a cation exchange resin in hydrogen ion form.

7. The method of claim 1 in which the eluent for the first resin column is an acid that improves the resolution of said anions.

8. The method of claim 1 in which the eluent of the first resin column is water.

9. The method of claim 1 in which said developing reagent comprises an ionized salt and said third resin column strips the cation of said salt at ion exchange sites to form substantially unionized molecules which are eluted from the column.

10. The method of claim 9 in which said developing reagent is an alkali metal carbonate or bicarbonate and said substantially unionized molecules are carbonic acid molecules.

11. The method of claim 9 in which said developing reagent comprises an acid and said substantially unionized molecules are water.

12. The method of claim 1 including after step (a) and prior to step (c), the following steps,
  (f) directing said first and second strong anionic species to a concentrator column including an anion exchange resin on which the anionic species are retained while the unretained solution associated with said anionic species passes through the concentrator column and is removed, whereby said first and second anionic species are concentrated prior to step (c), and
  (g) passing said developing reagent through said concentrator column to remove said first and second strong anionic species and carry them to the second resin column for performance of step (c).

13. The method of claim 12 in which step (f) is repeated at least once with additional sample prior to step (g) to supply additional quantities of said first and second strong anionic species to said concentrator column which are removed by said developing agent to further concentrate said anionic species for analysis.

14. The method of chromatographic separation and quantitative analysis of a plurality of anionic species in a sample solution, said method comprising
  (a) directing a sample of anionic species and an eluent through a first resin column, said first column containing a cationic or non-ionic chromatographic resin in a form to substantially resolve at least a first strong anionic species member from a group of anionic species including at least first and second weak anionic species members on elution from said column in said eluent,
  (b) directing the first and second weak anionic species and a highly ionized developing reagent solution through a second resin column, said second resin column containing a chromatographic anion exchange resin in a form to substantially resolve at least said first and second weak anionic species on elution from said second column,
  (c) directing said substantially resolved first and second weak anionic species to a third resin column, said third resin column containing a cation exchange resin of a type which substantially precludes passage of the developing reagent in highly ionized form and which permits passage of said resolved first and second weak anionic species without substantial interruption of the resolution, and
  (d) directing a solution of the resolved first and second weak anionic species from said third resin column through a conductivity cell having associated readout means and measuring the conductivity of said last named solution.

15. The method of claim 14 in which prior to step (b), the first and second weak anionic species are directed through an ion concentrator column including an anion exchange resin on which the weak anionic species are retained without substantial resolution while the unretained solution associated with said anionic species pass through the concentrator column and is removed, and then the developing reagent is passed through said concentrator column to remove said first and second weak anionic species and carry them to the chromatographic column of step (b) for performance of that step.

16. The method of chromatographic separation and quantitative analysis of a plurality of cationic species in a sample solution, said method comprising
  (a) directing a solution containing a plurality of cationic species and an eluent through a first resin column, said first column containing an anionic or non-ionic chromatographic resin in a form to substantially resolve at least a first weak cationic species, having a $pK_B$ value of about 2 to 7, from a group of ionic species including at least first and second strong cationic species members, having $pK_B$ values of about 0 to 2, on elution from said column in said eluent,
  (b) directing a solution of at least said substantially resolved first weak cationic species through a conductivity cell having associated readout means and measuring the conductivity of said last named solution,
  (c) directing the first and second strong cationic species and a highly ionized developing reagent solution through a second resin column, said second resin column containing a chromatographic anion exchange resin in a form to substantially resolve at least said first and second strong cationic species on elution from said second column,
  (d) directing said substantially resolved first and second strong cationic species to a third resin column, said third resin column containing an anion exchange resin of a type which substantially precludes passage of the developing reagent in highly ionized form and which permits passage of said resolved first and second strong cationic species without substantial interruption of the resolution, and
  (e) directing a solution of the resolved first and second strong cationic species from said third resin column through a conductivity cell having associated readout means and measuring the conductivity of said last named solution.

17. The method of claim 16 in which said sample solution includes at least a second weak cationic species.

18. The method of claim 17 together with the steps of:
  (f) separating said second weak cationic species together with said first weak cationic species from first and second strong cationic species in step (a),
  (h) directing said substantially resolved first and second weak cationic species to an anion exchange resin column of a type which substantially precludes passage of the developing reagent in highly ionized form and which permits passage of said resolved first and second weak cationic species without substantial interruption of the resolution, and (i) directing a solution of the resolved first and second weak cationic species through a conductivity cell having associated readout means and measuring the conductivity of said last named solution.

19. The method of claim 18 in which prior to step (g), the first and second weak cationic species are directed through an ion concentrator column including a cation exchange resin on which the cationic species are retained without substantial resolution while the untreated solution associated with said cationic species pass through the concentrator column and is removed, and then the developing reagent is passed through said concentrator column to remove said first and second weak cationic species and carry them to the chromatographic column of step (g) for performance of that step.

20. The method of claim 16 in which said first chromatographic column resin is in a form to substantially resolve said first and second strong cationic species, a solution of said resolved species is passed through a conductivity cell having associated readout means and the conductivity of the last named solution is measured.

21. The method of claim 16 in which the resin in the first resin column is an anion exchange resin in hydroxide ion form.

22. The method of claim 16 in which the eluent of the first resin column is water.

23. The method of claim 16 in which said developing reagent comprises an ionized salt and said third resin column strips the anion of said salt at ion exchange sites to form substantially unionized molecules which are eluted from the column.

24. The method of claim 16 including after step (a) and prior to step (c), the following steps, (f) directing said first and second strong cationic species to a concentrator column including a cation exchange resin on which the cationic species are retained while the unretained solution associated with said cationic species passes through the concentrator column and is removed, whereby said first and second cationic species are concentrated prior to step (c), and (g) passing said developing reagent through said concentrator column to remove said first and second strong cationic species and carry them to the second resin column for performance of step (c).

25. The method of claim 24 in which step (f) is repeated at least once with additional sample prior to step (g) to supply additional quantities of said first and second strong cationic species to said concentrator column which are removed by said developing agent to further concentrate said cationic species for analysis.

26. The method of chromatographic separation and quantitative analysis of a plurality of cationic species in a sample solution, said method comprising (a) directing said solution of cationic species and an eluent through a first resin column, said first column containing an anionic or non-ionic chromatographic resin in a form to substantially resolve at least a first strong cationic species member from a group of cationic species including at least first and second weak cationic species members on elution from said column in said eluent, (b) directing the first and second weak cationic species and a highly ionized developing reagent solution through a second resin column, said second resin column containing a chromatographic cation exchange resin in a form to substantially resolve at least said first and second weak cationic species on elution from said second column, (c) directing said substantially resolved first and second weak cationic species to a third resin column, said third resin column containing an anionic exchange resin of a type which substantially precludes passage of the developing reagent in highly ionized form and which permits passage of said resolved first and second weak cationic species without substantial interruption of the resolution, and (d) directing a solution of the resolved first and second weak cationic species from said third resin column through a conductivity cell having associated readout means and measuring the conductivity of said last named solution.

27. The method of claim 26 in which prior to step (b), the first and second weak cationic species are directed through an ion concentrator column including a cationic exchange resin on which the weak cationic species are retained without substantial resolution while the unretained solution associated with said cationic species pass through the concentrator column and is removed, and then the developing reagent is passed through said concentrator column to remove said first and second weak cationic species and carry them to the chromatographic column of step (b) for performance of that step.

* * * * *